(12) United States Patent
Liu et al.

(10) Patent No.: US 11,268,531 B2
(45) Date of Patent: Mar. 8, 2022

(54) FAN AND CONTROL METHOD THEREFOR

(71) Applicants: GD MIDEA ENVIRONMENT APPLIANCES MFG CO., LTD., Zhongshan (CN); MIDEA GROUP CO., LTD., Foshan (CN)

(72) Inventors: Jinquan Liu, Zhongshan (CN); Xinyun Pan, Zhongshan (CN)

(*) Notice: Subject to any disclaimer, the term of this patent is extended or adjusted under 35 U.S.C. 154(b) by 0 days.

(21) Appl. No.: 16/116,875

(22) Filed: Aug. 29, 2018

(65) Prior Publication Data
US 2018/0372108 A1 Dec. 27, 2018

Related U.S. Application Data

(63) Continuation of application No. PCT/CN2016/106304, filed on Nov. 17, 2016.

(30) Foreign Application Priority Data

Feb. 29, 2016 (CN) .......................... 201610116131.5

(51) Int. Cl.
*F04D 25/08* (2006.01)
*F04D 27/00* (2006.01)
(Continued)

(52) U.S. Cl.
CPC .......... *F04D 27/004* (2013.01); *F04D 25/08* (2013.01); *F24F 11/00* (2013.01); *F24F 11/30* (2018.01);
(Continued)

(58) Field of Classification Search
CPC .. F24F 11/66; F24F 11/62; F24F 11/56; F24F 11/59; F24F 11/61; F24F 2110/10; F04D 27/00; F04D 27/004
See application file for complete search history.

(56) References Cited

U.S. PATENT DOCUMENTS 5,634,346 A * 6/1997 Ramakrishnan ... G05D 23/1904
62/89
6,536,675 B1 * 3/2003 Pesko ..................... F24F 13/24
165/238
(Continued)

FOREIGN PATENT DOCUMENTS

| CN | 201827101 A | 5/2011 |
| CN | 102927028 A | 2/2013 |

(Continued)

OTHER PUBLICATIONS

CN First Office Action dated Apr. 1, 2017 in the corresponding CN application (application No. 201610116131.5).
(Continued)

*Primary Examiner* — Dominick L Plakkoottam
(74) *Attorney, Agent, or Firm* — Kilpatrick Townsend & Stockton, LLP

(57) ABSTRACT

A fan control method is described. The method includes obtaining, after controlling a fan to enter a scene wind running mode, the sleep time of a particular user corresponding to the scene wind running mode, obtaining a gear control time sequence of the fan according to the sleep time of the particular user, and controlling the fan according to the gear control time sequence of the fan to adjust the wind speed of the fan. The method can provide gentler wind during sleep of particular users such as babies and pregnant women to prevent the users from catching a cold, and also can provide a quitter sleep environment for babies and pregnant women to improve their sleep quality.

11 Claims, 5 Drawing Sheets

(51) Int. Cl.
    *F24F 11/66* (2018.01)
    *F24F 11/30* (2018.01)
    *F24F 11/00* (2018.01)
    *F24F 120/10* (2018.01)
    *F24F 110/00* (2018.01)
    *A61B 5/00* (2006.01)

(52) U.S. Cl.
    CPC ............. *F24F 11/66* (2018.01); *A61B 5/4809* (2013.01); *F24F 2110/00* (2018.01); *F24F 2120/10* (2018.01)

(56) References Cited

U.S. PATENT DOCUMENTS

| | | | | |
|---|---|---|---|---|
| 6,920,442 | B2* | 7/2005 | Lin | ...................... F24F 11/0001 706/45 |
| 6,968,707 | B2* | 11/2005 | Violand | .................. F24F 1/027 62/89 |
| 8,146,833 | B2* | 4/2012 | Song | ........................ F24F 11/30 236/46 C |
| 2006/0064996 | A1* | 3/2006 | Violand | .................. F24F 13/22 62/186 |
| 2006/0142968 | A1 | 6/2006 | Han et al. | |
| 2007/0032733 | A1 | 2/2007 | Burton | |
| 2008/0041075 | A1* | 2/2008 | Violand | .................. F24F 11/77 62/160 |
| 2009/0107498 | A1 | 4/2009 | Plattner et al. | |

FOREIGN PATENT DOCUMENTS

| | | |
|---|---|---|
| CN | 103822332 A | 5/2014 |
| CN | 104728146 A | 6/2015 |
| CN | 104806551 A | 7/2015 |
| CN | 105134633 A | 12/2015 |
| CN | 105318503 A | 2/2016 |
| CN | 105715575 A | 6/2016 |
| EP | 1810710 A1 | 7/2007 |
| JP | H07176956 A | 7/1995 |
| JP | H1122692 A | 1/1999 |
| JP | 6213936 B2 | 10/2017 |
| JP | 6241193 B2 | 12/2017 |
| TW | 512207 B | 12/2002 |
| WO | 2010087386 A1 | 8/2010 |
| WO | 2015141109 A1 | 9/2015 |

OTHER PUBLICATIONS

International Search Report dated Feb. 6, 2017 in the corresponding CN application (application No. PCT/CN2016/106304).
The second Office Action for JP Application 2018-545356.
The Office Action dated Aug. 6, 2019 in the corresponding JP application No. 2018-545356.
OA for EP application 16892363.9.

* cited by examiner

FAN AND CONTROL METHOD THEREFOR

CROSS-REFERENCE TO RELATED APPLICATIONS

This application is a continuation of International Application PCT/CN2016/106304, filed on Nov. 17, 2016, which claims priority to and the benefit of Chinese Patent Application No. 201610116131.5 filed with the Chinese Patent Office on Feb. 29, 2016, the entire contents of which are incorporated herein by reference.

FIELD

The present disclosure relates to a household appliance technology field, and more particularly to a fan control method and a fan.

BACKGROUND

In the related art, after a fan detects a child through a camera, the fan may enter a child mode, in which, a wind speed of the fan is adjusted via recognizing a distance between the child and the fan. When the distance between the child and the fan is relative small, the fan is stopped or powered off.

There may be certain defects in this method. When the camera fails, it is easy to have misidentification on the appearance feature recognition, which causes a problem that the fan can not enter the child mode, the control fails, and the wind speed control is not accurate due to inaccurate recognition of the distance from the child to the fan. In addition, when the distance between the fan and the child is relative small, the fan may be stopped or powered off, and aging of the control circuit and the motor may be accelerated due to the fan repeat switching between start and stop, which reduces the service life of the fan, and reduces the user experience.

SUMMARY

Embodiments of the present disclosure seek to solve at least one of the problems existing in the related art to at least some extent.

Accordingly, embodiments of the present disclosure is to provide a fan control method, which may provide soft wind for a specified user during a sleeping process of the user, thus effectively preventing the specified user from catching a cold due to cold wind, and may provide a quiet and comfortable sleeping environment for the specified user, improving sleeping quality of the specified user, with accurate control but without affecting the service life of the fan.

Another embodiment of the present disclosure is to provide a fan.

Embodiments of the present disclosure provide a fan control method, including: after the fan is controlled to enter a scene-wind operation mode, obtaining a sleeping time period of a specified user corresponding to the scene-wind operation mode; obtaining a control timing sequence for gears of the fan based on the sleeping time period of the specified user; and controlling the fan based on the control timing sequence for gears of the fan to adjust a speed of wind supplied by the fan.

With the fan control method according to embodiments of the present disclosure, after the fan is controlled to enter the scene-wind operation mode, the sleeping time period of the specified user corresponding to the scene-wind operation mode is obtained, the control timing sequence for gears of the fan is obtained based on the sleeping time period of the specified user, the fan is controlled based on the control timing sequence for gears of the fan to adjust the speed of wind supplied by the fan, thus providing soft wind for the specified user during the sleeping process of the user, effectively preventing the specified user from catching a cold due to cold wind, providing a quiet and comfortable sleeping environment for the specified user, and improving sleeping quality of the specified user, with accurate control but without affecting the service life of the fan.

In an embodiments of the present disclosure, obtaining the control timing sequence for gears of the fan based on the sleeping time period of the specified user includes: determining a sleeping state of the specified user based on the sleeping time period of the specified user, in which the sleeping state of the specified user comprises a light sleeping state and a deep sleeping state; when the specified user is in the light sleeping state, generating a first control timing sequence for gears by taking a user-set gear as a basic reference variable; and when the specified user is in the deep sleeping state, generating a second control timing sequence for gears according to the first control timing sequence for gears control.

In an embodiments of the present disclosure, when the specified user is in the light sleeping state, controlling the fan based on the first control timing sequence for gears includes: when the sleeping time period of the specified user reaches a first preset sleeping time period, controlling the fan to operate in a second gear of wind speed, controlling the fan to operate in a third gear of wind speed after the fan is controlled to operate in the second gear of wind speed for a first preset time period, controlling the fan to operate in the second gear of wind speed for the first preset time period after the fan is controlled to operate in the third gear of wind speed for the first preset time period, repeating the controlling process until the sleeping time period of the specified user reaches a second preset sleeping time period; when the sleeping time period of the specified user reaches the second preset sleeping time period, controlling the fan to operate in the second gear of wind speed, controlling the fan to operate in the third gear of wind speed after the fan is controlled to operate in the second gear of wind speed for a second preset time period, controlling the fan to operate in a first gear of wind speed after the fan is controlled to operate in the third gear of wind speed for the second preset time period, and controlling the fan to operate in the first gear of wind speed again after the fan is controlled to operate in the first gear of wind speed for the second preset time period, repeating the controlling process until the sleeping time period of the specified user reaches a third preset sleeping time period, in which the second gear of wind speed is greater than the first gear of wind speed and is smaller than the third gear of wind speed.

Further, after the sleeping time period of the specified user reaches the first preset sleeping time period, the method includes: controlling the fan to rotate based on a first preset angle.

In an embodiments of the present disclosure, when the specified user is in the deep sleeping state, controlling the fan based on the second control timing sequence for gears includes: controlling the fan to operate in a second gear of wind speed after the fan is controlled to operate in a first gear of wind speed for a third preset time period, controlling the fan to operate in the first gear of wind speed for the third preset time period after the fan is controlled to operate in the second gear of wind speed for the third preset time period, repeating the controlling process until the sleeping time period of the specified user reaches a fourth preset sleeping time period; when the sleeping time period of the specified user reaches the fourth preset sleeping time period, controlling the fan to operate in the second gear of wind speed, controlling the fan to operate in the second gear of wind speed after the fan is controlled to operate in the second gear of wind speed for a fourth preset time period, controlling the fan to operate in the first gear of wind speed for the fourth preset time period after the fan is controlled to operate in the second gear of wind speed for the fourth preset time period, repeating the controlling process until the sleeping time period of the specified user reaches a fifth preset sleeping time period; when the sleeping time period of the specified user reaches the fifth preset sleeping time period, controlling the fan to operate in the first gear of wind speed, controlling the fan to operate in the second gear of wind speed after the fan is controlled to operate in the first gear of wind speed for a fifth preset time period, controlling the fan to operate in the first gear of wind speed after the fan is controlled to operate in the second gear of wind speed for the fifth preset time period, and controlling the fan to operate in the first gear of wind speed again after the fan is controlled to operate in the first gear of wind speed for the fifth preset time period, repeating the controlling process until the sleeping time period of the specified user reaches a sixth preset sleeping time period, in which the second gear of wind speed is greater than the first gear of wind speed.

Further, after the sleeping time period of the specified user reaches the first preset sleeping time period, the method includes: controlling the fan to rotate based on a second preset angle, and controlling the fan to remain operating in the first gear of wind speed.

In an embodiments of the present disclosure, the method further includes: when the specified user is awake from the sleeping state, controlling the fan to operate in a first gear of wind speed, controlling the fan to operate in a third gear of wind speed after the fan is controlled to operate in the first gear of wind speed for a sixth preset time period, and controlling the fan to operate in a second gear of wind speed for the sixth preset time period after the fan is controlled to operate in the third gear of wind speed for the sixth preset time period, repeating the controlling process until a waking time period of the specified user reaches a first preset waking time period; when the waking time period of the specified user reaches the first preset waking time period, controlling the fan to operate in the second gear of wind speed, controlling the fan to operate in the third gear of wind speed after the fan is controlled to operate in the second gear of wind speed for a seventh preset time period, controlling the fan to operate in the first gear of wind speed after the fan is controlled to operate in the third gear of wind speed for the seventh preset time period, and controlling the fan to operate in the first gear of wind speed again after the fan is controlled to operate in the first gear of wind speed for the seventh preset time period, repeating the controlling process until the fan receives a power-off instruction and the fan is powered off, in which the second gear of wind speed is greater than the first gear of wind speed and is smaller than the third gear of wind speed.

In an embodiments of the present disclosure, after the specified user is awake from the sleeping state, the method further includes: controlling the fan to rotate based on a third preset angle.

In an embodiments of the present disclosure, the speed of wind supplied by the fan is greater than or equal to 30 revolutions/minute and is smaller than or equal to 180 revolutions/minute.

In an embodiments of the present disclosure, the method further includes: obtaining a human parameter of the specified user, and generating a wind speed adjusting instruction and a fan-rotating adjusting instruction based on the human parameter of the specified user to adjust the speed of wind supplied by the fan and a rotation angle of the fan.

In an embodiments of the present disclosure, the method further includes: obtaining image information of the specified user, obtaining the sleeping state and sleeping quality of the specified user based on the image information of the specified user, and modifying the control timing sequence for gears of the fan based on the sleeping state and the sleeping quality of the specified user.

Further, the method includes: sending the sleeping state and the sleeping quality of the specified user to a mobile terminal.

Further, the method includes: obtaining speech information of the specified user, sending the speech information of the specified user to the mobile terminal, and receiving speech information from the mobile terminal.

In an embodiments of the present disclosure, when controlling the fan based on the control timing sequence for gears of the fan, the speed of wind supplied by the fan is controlled based on a formula of:

$$h(t) = 1 - \frac{1}{\sqrt{1-\zeta^2}} e^{-\delta} \sin\left[\sqrt{1-\zeta^2}\, \omega_n t + \arccos\zeta\right]$$

where, h(t) is a response function, δ is an attenuation index, ξ is a damping ratio, $\omega_n$ is an undamped oscillation frequency, and t is time.

Embodiments of the present disclosure provide a fan, including: fan blades; a motor, configured to drive the fan blades to rotate; and a main control device, configured to, after the fan is controlled to enter a scene-wind operation mode, obtain a sleeping time period of a specified user corresponding to the scene-wind operation mode, to obtain a control timing sequence for gears of the fan based on the sleeping time period of the specified user, and to control the fan based on the control timing sequence for gears of the fan to adjust a speed of wind supplied by the fan.

With the fan according to embodiments of the present disclosure, after controlling the fan to enter the scene-wind operation mode, the main control device obtains the sleeping time period of the specified user corresponding to the scene-wind operation mode, obtains the control timing sequence for gears of the fan based on the sleeping time period of the specified user, and controls the fan based on the control timing sequence for gears of the fan to adjust the speed of wind supplied by the fan, thus providing soft wind for the specified user during the sleeping process of the user, effectively preventing the specified user from catching a cold due to cold wind, providing a quiet and comfortable sleeping environment for the specified user, and improving sleeping quality of the specified user, with accurate control but without affecting the service life of the fan.

In an embodiments of the present disclosure, when the main control device is configured to obtain the control timing sequence for gears of the fan based on the sleeping time period of the specified user, the main control device is configured to determine a sleeping state of the specified user based on the sleeping time period of the specified user, and the sleeping state of the specified user comprises a light sleeping state and a deep sleeping state, when the specified user is in the light sleeping state, the main control device is configured to generate a first control timing sequence for gears by taking a user-set gear as a basic reference variable, when the specified user is in the deep sleeping state, the main control device is configured to generate a second control timing sequence for gears according to the first control timing sequence for gears.

In an embodiments of the present disclosure, when the specified user is in the light sleeping state, and the main control device is configured to control the fan based on the first control timing sequence for gears, when the sleeping time period of the specified user reaches a first preset sleeping time period, the main control device is configured to control the fan to operate in a second gear of wind speed, to control the fan to operate in a third gear of wind speed after the fan is controlled to operate in the second gear of wind speed for a first preset time period, to control the fan to operate in the second gear of wind speed for the first preset time period after the fan is controlled to operate in the third gear of wind speed for the first preset time period, and to repeat the controlling process until the sleeping time period of the specified user reaches a second preset sleeping time period; when the sleeping time period of the specified user reaches the second preset sleeping time period, the main control device is configured to control the fan to operate in the second gear of wind speed, to control the fan to operate in the third gear of wind speed after the fan is controlled to operate in the second gear of wind speed for a second preset time period, to control the fan to operate in a first gear of wind speed after the fan is controlled to operate in the third gear of wind speed for the second preset time period, and to control the fan to operate in the first gear of wind speed again after the fan is controlled to operate in the first gear of wind speed for the second preset time period, and repeat the controlling process until the sleeping time period of the specified user reaches a third preset sleeping time period, in which the second gear of wind speed is greater than the first gear of wind speed and is smaller than the third gear of wind speed.

Further, after the sleeping time period of the specified user reaches the first preset sleeping time period, the main control device is configured to control the fan to rotate based on a first preset angle.

In an embodiments of the present disclosure, when the specified user is in the deep sleeping state, and the main control device is configured to control the fan based on the second control timing sequence for gears, the main control device is configured to control the fan to operate in a second gear of wind speed after the fan is controlled to operate in a first gear of wind speed for a third preset time period, to control the fan to operate in the first gear of wind speed for the third preset time period after the fan is controlled to operate in the second gear of wind speed for the third preset time period, to repeat the controlling process until the sleeping time period of the specified user reaches a fourth preset sleeping time period; when the sleeping time period of the specified user reaches the fourth preset sleeping time period, the main control device is configured to control the fan to operate in the second gear of wind speed, to control the fan to operate in the second gear of wind speed after the fan is controlled to operate in the second gear of wind speed for a fourth preset time period, to control the fan to operate in the first gear of wind speed for the fourth preset time period after the fan is controlled to operate in the second gear of wind speed for the fourth preset time period, and to repeat the controlling process until the sleeping time period of the specified user reaches a fifth preset sleeping time period; when the sleeping time period of the specified user reaches the fifth preset sleeping time period, the main control device is configured to control the fan to operate in the first gear of wind speed, to control the fan to operate in the second gear of wind speed after the fan is controlled to operate in the first gear of wind speed for a fifth preset time period, to control the fan to operate in the first gear of wind speed after the fan is controlled to operate in the second gear of wind speed for the fifth preset time period, and to control the fan to operate in the first gear of wind speed again after the fan is controlled to operate in the first gear of wind speed for the fifth preset time period, and to repeat the controlling process until the sleeping time period of the specified user reaches a sixth preset sleeping time period, in which the second gear of wind speed is greater than the first gear of wind speed.

Further, after the sleeping time period of the specified user reaches the sixth preset sleeping time period, the main control device is configured to control the fan to rotate based on a second preset angle, and to control the fan to remain operating in the first gear of wind speed.

In an embodiments of the present disclosure, when the specified user is awake from the sleeping state, the main control device is configured to control the fan to operate in a first gear of wind speed, to control the fan to operate in a third gear of wind speed after the fan is controlled to operate in the first gear of wind speed for a sixth preset time period, and to control the fan to operate in a second gear of wind speed for the sixth preset time period after the fan is controlled to operate in the third gear of wind speed for the sixth preset time period, and to repeat the controlling process until the sleeping time period of the specified user reaches a first preset sleeping time period; when the sleeping time period of the specified user reaches the first preset sleeping time period, the main control device is configured to control the fan to operate in the second gear of wind speed, to control the fan to operate in the third gear of wind speed after the fan is controlled to operate in the second gear of wind speed for a seventh preset time period, to control the fan to operate in the first gear of wind speed after the fan is controlled to operate in the third gear of wind speed for the seventh preset time period, and to control the fan to operate in the first gear of wind speed again after the fan is controlled to operate in the first gear of wind speed for the seventh preset time period, and to repeat the controlling process until the fan receives a power-off instruction and the fan is powered off, in which the second gear of wind speed is greater than the first gear of wind speed and is smaller than the third gear of wind speed.

Further, after the specified user is awake from the sleeping state, the main control device is configured to the fan to rotate based on a third preset angle.

In an embodiments of the present disclosure, the speed of wind supplied by the fan is greater than or equal to 30 revolutions/minute and is smaller than or equal to 180 revolutions/minute.

In an embodiments of the present disclosure, the fan further includes: a somatosensory obtaining device, configured to obtain a human parameter of the specified user, and the main control device is configured to generate a wind speed adjusting instruction and a fan-rotating adjusting instruction based on the human parameter of the specified user to adjust the speed of wind supplied by the fan and a rotation angle of the fan.

In an embodiments of the present disclosure, the fan further includes: a camera, configured to obtain image information of the specified user, and the main control device is configured to obtain the sleeping state and sleeping quality of the specified user based on the image information of the specified user, and to modify the control timing sequence for gears of the fan based on the sleeping state and the sleeping quality of the specified user.

Further, the fan includes: a communication device, configured to send the sleeping state and the sleeping quality of the specified user to a mobile terminal.

Further, the fan includes: a speech obtaining device, configured to obtain speech information of the specified user, and the main control device is configured to send the speech information of the specified user to the mobile terminal via the communication device, and to receive speech information from the mobile terminal via the communication device.

In an embodiments of the present disclosure, when the main control device is configured to control the fan based on the control timing sequence for gears of the fan, the main control device is configured to control the speed of wind supplied by the fan based on a formula of:

$$h(t) = 1 - \frac{1}{\sqrt{1-\zeta^2}} e^{-\delta} \sin\left[\sqrt{1-\zeta^2}\, \omega_n t + \arccos\zeta\right]$$

where, h(t) is a response function, δ is an attenuation index, ξ is a damping ratio, $\omega_n$ is an undamped oscillation frequency, t is time.

DETAILED DESCRIPTION

Figure 1:
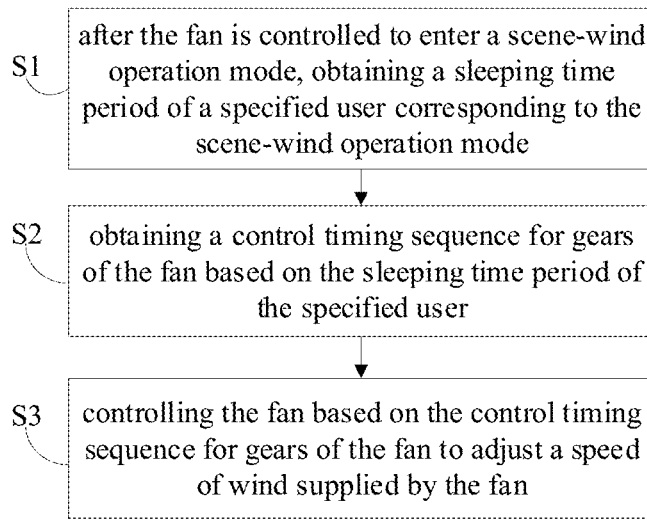
FIG. 1 is a flow chart of the fan control method according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

In the following, a fan control method and a fan provided according to embodiments of the present disclosure are described with reference to drawings FIG. 1 is a flow chart of the fan control method according to an embodiment of the present disclosure. As illustrated in FIG. 1, the fan control method includes follows.

At block S1, after the fan is controlled to enter a scene-wind operation mode, a sleeping time period of a specified user corresponding to the scene-wind operation mode is obtained. The specified user may refer to a special group such as a baby, a pregnant woman, or the like.

In detail, when the specified user such as a baby begins to sleep, parents of the baby or the like may control the fan to enter the scene-wind operation mode via a button, a remote control, a mobile terminal or the like. The remote control may communicate with the fan via wireless communication methods, such as infrared, radio frequency, WiFi.

At block S2, obtaining a control timing sequence for gears of the fan based on the sleeping time period of the specified user.

In an embodiment of the present disclosure, obtaining the control timing sequence for gears of the fan based on the sleeping time period of the specified user includes: determining a sleeping state of the specified user based on the sleeping time period of the specified user, in which the sleeping state of the specified user includes a light sleeping state and a deep sleeping state; when the specified user is in the light sleeping state, generating a first control timing sequence for gears by taking a user-set gear as a basic reference variable; and when the specified user is in the deep sleeping state, generating a second control timing sequence for gears according to the first control timing sequence for gears control.

In detail, when the specified user such as the baby enters sleep, the light sleeping state may be first entered, and then the deep sleeping state may be entered. When the baby begins to sleep, the parents and the like of the baby may control the fan to enter the scene-wind operation mode via the button, the remote control, the mobile terminal or the like, and an initial gear of the fan is set. At the same time, the fan may generate the first timing sequence for gears and the second timing sequence for gears by taking the user-set gear as the basic reference variable, and then the fan is controlled according to the first timing sequence for gears and the second timing sequence for gears to adjust the speed of wind supplied by the fan, thus providing soft, comfortable wind speed for the baby during sleeping process of the baby, preventing the baby from catching a cold, and ensuring the baby to have a well sleeping environment.

At block S3, the fan is controlled based on the control timing sequence for gears of the fan to adjust a speed of wind supplied by the fan.

In an embodiment of the present disclosure, when the specified user is in the light sleeping state, controlling the fan based on the first control timing sequence for gears includes: when the sleeping time period of the specified user reaches a first preset sleeping time period, controlling the fan to operate in a second gear of wind speed, controlling the fan to operate in a third gear of wind speed after the fan is controlled to operate in the second gear of wind speed for a first preset time period, controlling the fan to operate in the second gear of wind speed for the first preset time period after the fan is controlled to operate in the third gear of wind speed for the first preset time period, repeating the controlling process until the sleeping time period of the specified user reaches a second preset sleeping time period; and when the sleeping time period of the specified user reaches the second preset sleeping time period, controlling the fan to operate in the second gear of wind speed, controlling the fan to operate in the third gear of wind speed after the fan is controlled to operate in the second gear of wind speed for a second preset time period, controlling the fan to operate in a first gear of wind speed after the fan is controlled to operate in the third gear of wind speed for the second preset time period, and controlling the fan to operate in the first gear of wind speed again after the fan is controlled to operate in the first gear of wind speed for the second preset time period, repeating the controlling process until the sleeping time period of the specified user reaches a third preset sleeping time period. The second gear of wind speed is greater than the first gear of wind speed and is smaller than the third gear of wind speed.

In addition, after the sleeping time period of the specified user reaches the first preset sleeping time period, the fan is controlled to rotate based on a first preset angle.

Figure 2A:
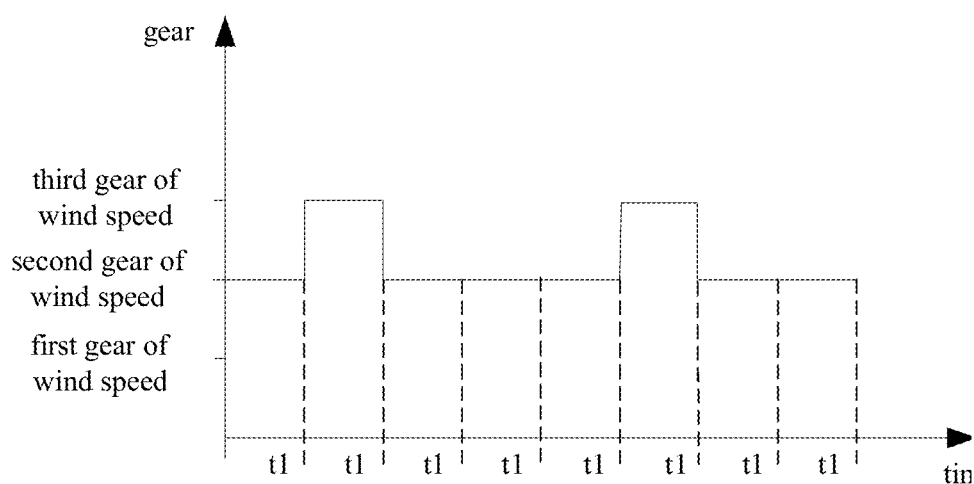
FIG. 2a-2b are schematic diagrams illustrating a first control timing sequence for gears according to an embodiment of the present disclosure.
Figure 2B:
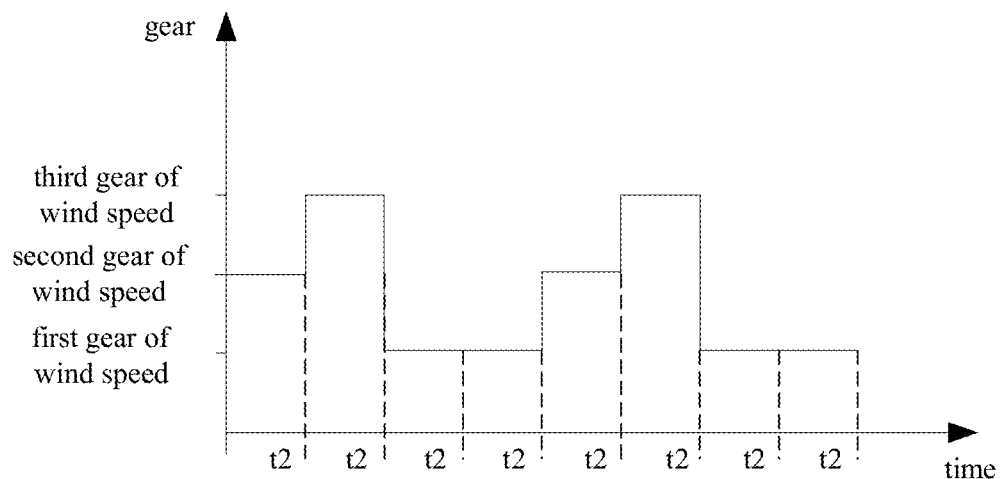

In detail, when the specified user such as the baby sleeps for 10-20 minutes since the baby begins to sleep, i.e., the sleeping time period of the baby reaches the first preset sleeping time period, the fan enters the first control timing sequence for gears. As illustrated in FIG. 2a, the fan is first controlled to operate in the second gear of wind speed for the first preset time period $\Delta t1$, then the fan is controlled to operate in the third gear of wind speed for the first preset time period $\Delta t1$, then the fan is controlled to operate in the second gear of wind speed for the first preset time period $\Delta t1$, then the fan is controlled to operate in the second gear of wind speed for the first preset time period $\Delta t1$, . . . , these processes are repeated until the sleeping time period of the baby reaches the second preset sleeping time period such as 1 hour and 30 minutes. Then, as illustrated in FIG. 2b, the fan is controlled to operate in the second gear of wind speed for the second preset time period $\Delta t2$, then the fan is controlled to operate in the third gear of wind speed for the second preset time period $\Delta t2$, then the fan is controlled to operate in the first gear of wind speed for the second preset time period $\Delta t2$, and then the fan is controlled to operate in the first gear of wind speed for the second preset time period $\Delta t2$, . . . , these processes are repeated, and the fan is controlled to rotate based on the first preset angle such as 90°, until the sleeping time period of the baby reaches the third preset sleeping time period, such as 2 hours and 30 minutes. The first preset time period $\Delta t1$ and the second preset time period $\Delta t2$ may be the same, for example, may be 15 seconds.

In an embodiment of the present disclosure, when the specified user is in the deep sleeping state, controlling the fan based on the second control timing sequence for gears includes: controlling the fan to operate in a second gear of wind speed after the fan is controlled to operate in a first gear of wind speed for a third preset time period, controlling the fan to operate in the first gear of wind speed for the third preset time period after the fan is controlled to operate in the second gear of wind speed for the third preset time period, repeating the controlling process until the sleeping time period of the specified user reaches a fourth preset sleeping time period; when the sleeping time period of the specified user reaches the fourth preset sleeping time period, controlling the fan to operate in the second gear of wind speed, controlling the fan to operate in the second gear of wind speed after the fan is controlled to operate in the second gear of wind speed for a fourth preset time period, controlling the fan to operate in the first gear of wind speed for the fourth preset time period after the fan is controlled to operate in the second gear of wind speed for the fourth preset time period, repeating the controlling process until the sleeping time period of the specified user reaches a fifth preset sleeping time period; when the sleeping time period of the specified user reaches the fifth preset sleeping time period, controlling the fan to operate in the first gear of wind speed, controlling the fan to operate in the second gear of wind speed after the fan is controlled to operate in the first gear of wind speed for a fifth preset time period, controlling the fan to operate in the first gear of wind speed after the fan is controlled to operate in the second gear of wind speed for the fifth preset time period, and controlling the fan to operate in the first gear of wind speed again after the fan is controlled to operate in the first gear of wind speed for the fifth preset time period, repeating the controlling process until the sleeping time period of the specified user reaches a sixth preset sleeping time period. The second gear of wind speed is greater than the first gear of wind speed.

In addition, after the sleeping time period of the specified user reaches the sixth preset sleeping time period, the fan is controlled to rotate based on a second preset angle, and the fan is controlled to remain operating in the first gear of wind speed.

Figure 3A:
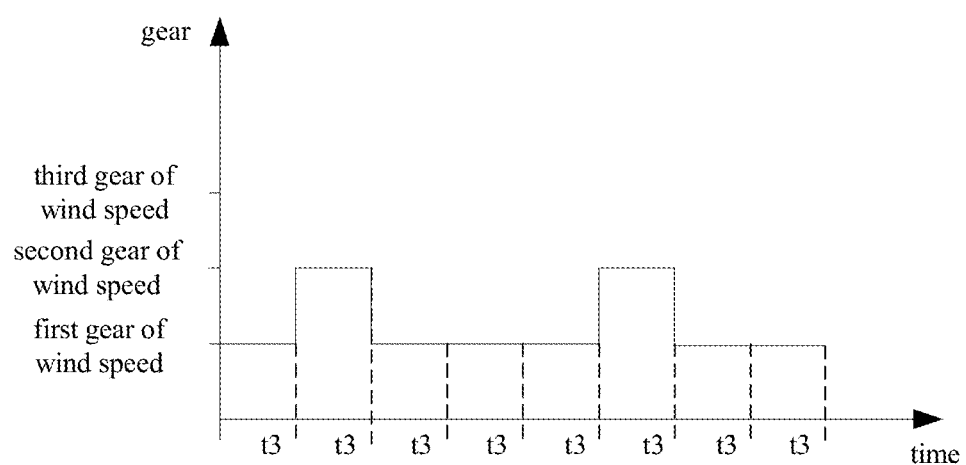
FIG. 3a-3c are schematic diagrams illustrating a second control timing sequence for gears according to an embodiment of the present disclosure.
Figure 3B:
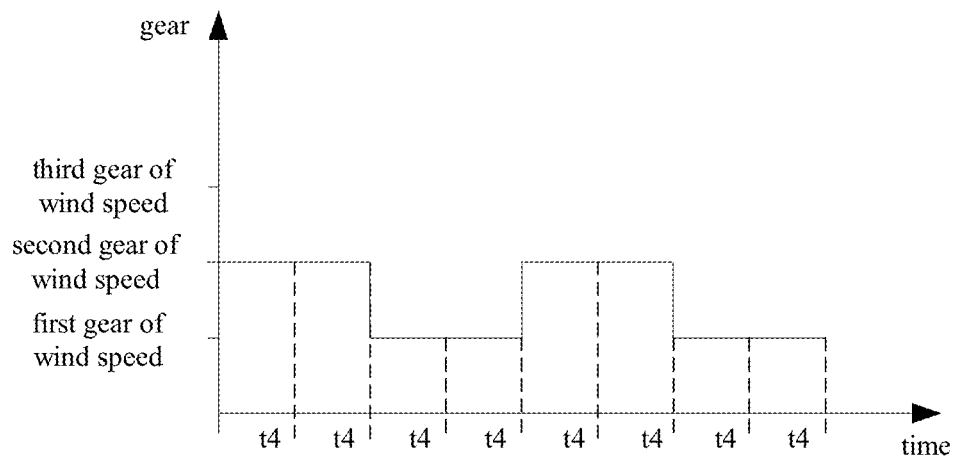
Figure 3C:
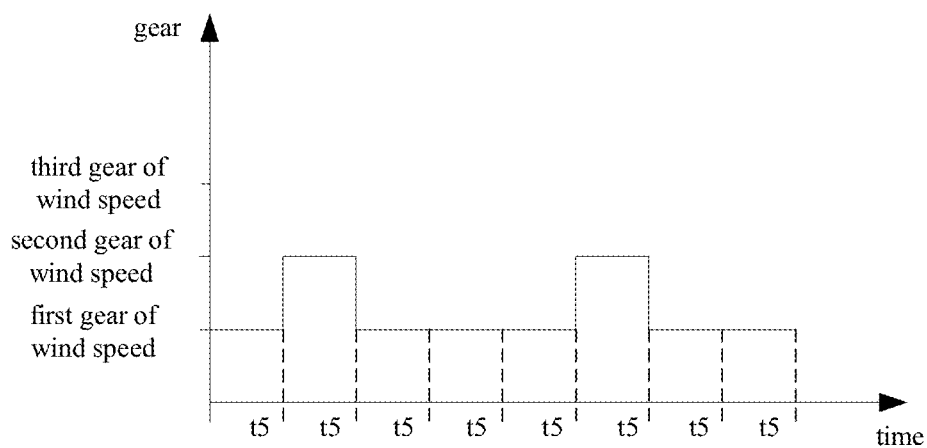

In detail, when the specified user such as the baby enters the deep sleeping state, for example, the sleeping time period of the baby reaches the third preset sleeping time period, such as 2 hours and 30 minutes, as illustrated in FIG. 3a the fan is first controlled to operate in the first gear of wind speed for the third preset time period $\Delta t3$, then the fan is controlled to operate in the second gear of wind speed for the third preset time period $\Delta t3$, then the fan is controlled to operate in the first gear of wind speed for the third preset time period $\Delta t3$, then the fan is controlled to operate in the first gear of wind speed for the third preset time period $\Delta t3$, . . . , these processes are repeated until the sleeping time period of the baby reaches the fourth preset sleeping time period such as 3 hour and 20 minutes. Then, as illustrated in FIG. 3b, the fan is controlled to operate in the second gear of wind speed for the fourth preset time period $\Delta t4$, then the fan is controlled to operate in the second gear of wind speed for the fourth preset time period $\Delta t4$, then the fan is controlled to operate in the first gear of wind speed for the fourth preset time period $\Delta t4$, and then the fan is controlled to operate in the first gear of wind speed for the fourth preset time period $\Delta t4$, . . . , these processes are repeated until the sleeping time period of the baby reaches the fifth preset sleeping time period such as 4 hour and 10 minutes. And then, as illustrated in FIG. 3c, the fan is controlled to operate in the first gear of wind speed for the fifth preset time period $\Delta t5$, then the fan is controlled to operate in the second gear of wind speed for the fifth preset time period $\Delta t5$, then the fan is controlled to operate in the first gear of wind speed for the fifth preset time period $\Delta t5$, and then the fan is controlled to operate in the first gear of wind speed for the fifth preset time period $\Delta t5$, . . . , these processes are repeated for 30 minutes. That is, after the sleeping time period of the baby reaches the sixth preset sleeping time period such as 4 hour and 40 minutes, the fan is controlled to rotate based on the second preset angle such as 120°, and the fan is controlled to remain operating in the first gear of wind speed until the baby wakes up from the sleeping state. The third preset time period $\Delta t3$, the fourth preset time period $\Delta t4$, and the fifth preset time period $\Delta t5$ may be the same, for example, may be 15 seconds.

In an embodiment of the present disclosure, when the specified user is awake from the sleeping state, the method further includes: controlling the fan to operate in a first gear of wind speed, controlling the fan to operate in a third gear of wind speed after the fan is controlled to operate in the first gear of wind speed for a sixth preset time period, and controlling the fan to operate in a second gear of wind speed for the sixth preset time period after the fan is controlled to operate in the third gear of wind speed for the sixth preset time period, repeating the controlling process until a waking time period of the specified user reaches a first preset waking time period; when the waking time period of the specified user reaches the first preset waking time period, controlling the fan to operate in the second gear of wind speed, controlling the fan to operate in the third gear of wind speed after the fan is controlled to operate in the second gear of wind speed for a seventh preset time period, controlling the fan to operate in the first gear of wind speed after the fan is controlled to operate in the third gear of wind speed for the seventh preset time period, and controlling the fan to operate in the first gear of wind speed again after the fan is controlled to operate in the first gear of wind speed for the seventh preset time period, repeating the controlling process until the fan receives a power-off instruction and the fan is powered off. The second gear of wind speed is greater than the first gear of wind speed and is smaller than the third gear of wind speed.

In addition, after the specified user is awake from the sleeping state, the fan is controlled to rotate based on a third preset angle.

Figure 4A:
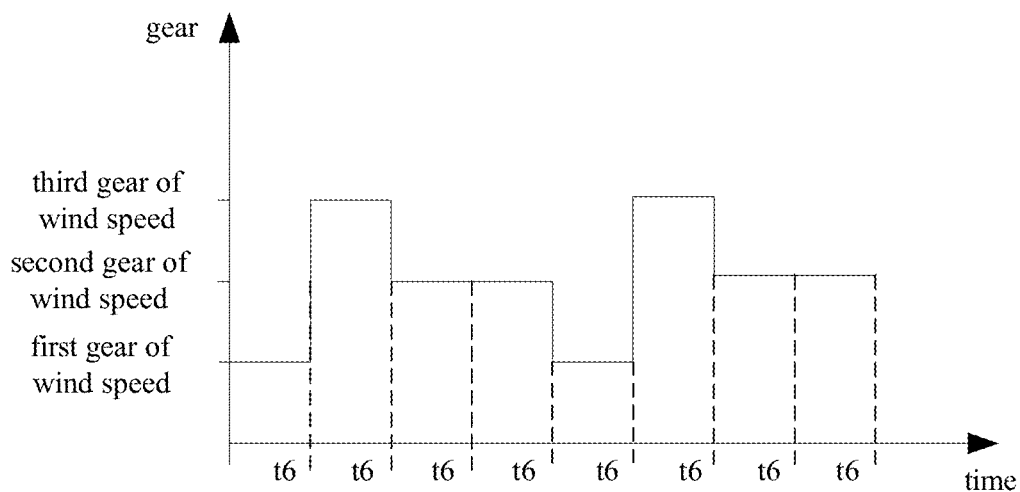
FIG. 4a-4b are schematic diagrams illustrating a control timing sequence for gears after a specified user wakes up according to an embodiment of the present disclosure.
Figure 4B:
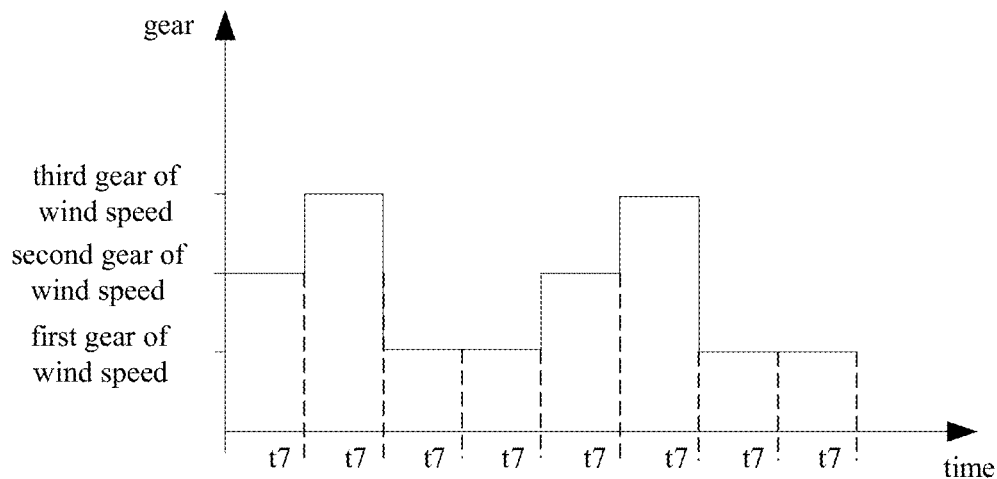

In detail, when the specified user such as the baby is awake from the sleeping state, as illustrated in FIG. 4a, the fan is first controlled to operate in the first gear of wind speed for the sixth preset time period Δt6, then the fan is controlled to operate in the third gear of wind speed for the sixth preset time period Δt6, then the fan is controlled to operate in the second gear of wind speed for the sixth preset time period Δt6, then the fan is controlled to operate in the second gear of wind speed for the sixth preset time period Δt6, . . . , these processes are repeated until the waking time period of the baby reaches the first preset waking time period such as 1 hour and 30 minutes. Then, as illustrated in FIG. 4b, the fan is controlled to operate in the second gear of wind speed for the seventh preset time period Δt7, then the fan is controlled to operate in the third gear of wind speed for the seventh preset time period Δt7, then the fan is controlled to operate in the first gear of wind speed for the seventh preset time period Δt7, and then the fan is controlled to operate in the first gear of wind speed for the seventh preset time period Δt7, . . . , these processes are repeated, and the fan is controlled to rotate based on the third preset angle such as 90°, until the fan is powered off. The sixth preset time period Δt6 and the seventh preset time period Δt7 may be the same, for example, may be 10 seconds.

In some embodiments of the present disclosure, the speed of wind supplied by the fan is greater than or equal to 30 revolutions/minute and is smaller than or equal to 180 revolutions/minute.

Further, in some embodiments of the present disclosure, a speed of wind supplied by the fan corresponding to the first gear of wind speed may be greater than or equal to 30 revolutions/minute and is smaller than or equal to 50 revolutions/minute. A speed of wind supplied by the fan corresponding to the second gear of wind speed may be greater than or equal to 50 revolutions/minute and is smaller than or equal to 100 revolutions/minute. A speed of wind supplied by the fan corresponding to the third gear of wind speed may be greater than or equal to 100 revolutions/minute and is smaller than or equal to 180 revolutions/minute. For example, a direct current frequency conversion motor in the fan may be controlled by a rotation speed closed loop control mode to realize the quick start and low speed closed loop control of the fan, and the speed of wind supplied by the fan is compensated by the low speed torque compensation algorithm to ensure stability of the speed of wind supplied by the fan. The direct current frequency conversion motor has advantages of low loss and low noise, thus it may provide the specified user with good sleeping environment, so that the specified user may sleep sweetly.

In addition, when controlling the fan based on the control timing sequence for gears of the fan, the speed of wind supplied by the fan is controlled based on a following formula:

$$h(t) = 1 - \frac{1}{\sqrt{1-\zeta^2}} e^{-\delta} \sin\left[\sqrt{1-\zeta^2}\,\omega_n t + \arccos\zeta\right] \quad (1)$$

where, h(t) is a response function, δ is an attenuation index, ξ is a damping ratio, $\omega_n$ is an undamped oscillation frequency, and t is time.

Figure 5:
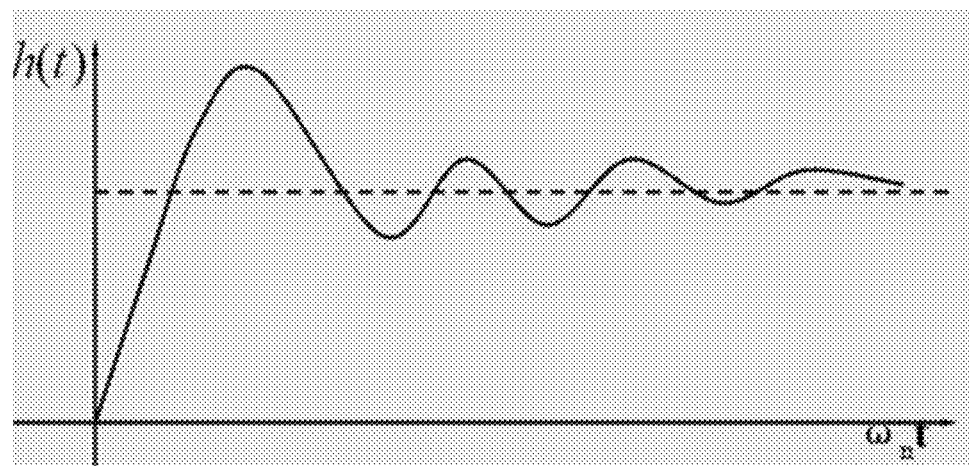
FIG. 5 is a block diagram illustrating a damped oscillation curve according to an embodiment of the present disclosure.

That is, the speed of wind supplied by the fan is controlled based on a damped oscillation curve control algorithm. A corresponding damped oscillation curve may be illustrated in FIG. 5.

The direct current frequency conversion motor is controlled based on the damped oscillation curve control algorithm, so that the speed of wind supplied by the fan is close to a speed of wind shook by a user. That is, a slight wind control is realized, giving comfortable and cool feeling to the specified user such as the baby, the pregnant woman and the like, greatly reducing a probability of catching a cold for the specified user, and low power operation of the direct current frequency conversion motor is realized, achieving effect of energy saving and extending service life.

In an embodiment of the present disclosure, the above-mentioned fan control method further includes: obtaining a human parameter of the specified user, and generating a wind speed adjusting instruction and a fan-rotating adjusting instruction based on the human parameter of the specified user to adjust the speed of wind supplied by the fan and a rotation angle of the fan.

The human parameter may include body temperature, expression, impatience degree, status, etc. of the specified user. The speed of wind supplied by the fan and the rotation angle of the fan are finely adjusted based on the body parameter of the specified user, so that the speed of wind supplied by the fan and the rotation angle are close to actual needs of the specified user, thereby improving the comfort of the specified user. For example, when the baby is crying, the rotation angle of the fan may be adjusted, such as adjusted between 30° and 180°, to keep the baby away from the fan, and the speed of wind supplied by the fan is adjusted to ensure that the baby may not sweat when crying, not catch a cold, achieving self-adaptation.

In an embodiment of the present disclosure, the above-mentioned fan control method further includes: obtaining image information of the specified user, obtaining the sleeping state and sleeping quality of the specified user based on the image information of the specified user, and modifying the control timing sequence for gears of the fan based on the sleeping state and the sleeping quality of the specified user. Further, the above-mentioned fan control method further includes: sending the sleeping state and the sleeping quality of the specified user to a mobile terminal.

In detail, the image information of the specified user such as the baby may be collected via a camera. The sleeping state and sleeping quality of the baby is obtained by performing comparison analysis on the image information. The control timing sequence for gears of the fan is modified based on the sleeping state and the sleeping quality of the baby. The fan is controlled according to the modified control timing sequence for gears. At the same time, the sleeping state and sleeping quality of the baby may be sent to the mobile terminal, such as a mobile phone, of parents and the like of the baby. The image information of the baby may also be directly sent to the mobile terminal to realize video sharing, so that the parents and the like of the baby may remotely acknowledge information about the baby in real time, thus the parents and the like of the baby may be more reassured.

In an embodiment of the present disclosure, the above-mentioned fan control method further includes: obtaining speech information of the specified user, sending the speech information of the specified user to the mobile terminal, and receiving speech information from the mobile terminal.

In detail, sound of the specified user may be obtained by a microphone during the sleeping process. The sound of the specified user is sent to a mobile terminal such as a mobile phone of a person relative to the specified user. For example, when the specified user such as the baby wakes up, the baby may call its parents, at this time, the sound of the baby may be sent to the mobile terminal such as the mobile phone of persons such the parents of the baby or the like. The parents such the parents of the baby or the like may talk to the baby after the parents of the baby or the like receives the call of the baby, to take care of the baby remotely.

With the fan control method according to embodiments of the present disclosure, after the fan is controlled to enter the scene-wind operation mode, the sleeping time period of the specified user corresponding to the scene-wind operation mode is obtained, the control timing sequence for gears of the fan is obtained based on the sleeping time period of the specified user, the fan is controlled based on the control timing sequence for gears of the fan to adjust the speed of wind supplied by the fan, thus providing soft wind for the specified user during the sleeping process of the user, effectively preventing the specified user from catching a cold due to cold wind, providing a quiet and comfortable sleeping environment for the specified user, and improving sleeping quality of the specified user, with accurate control but without affecting the service life of the fan.

Figure 6:
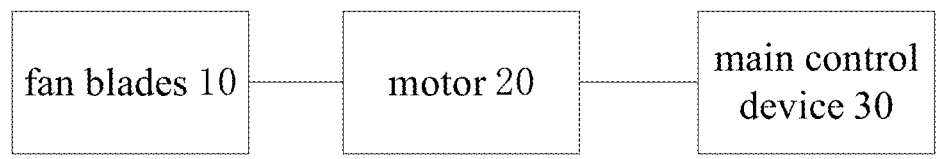
FIG. 6 is a block diagram illustrating a fan according to an embodiment of the present disclosure.

FIG. 6 is a block diagram illustrating a fan according to an embodiment of the present disclosure. As illustrated in FIG. 6, the fan includes fan blades 10, a motor 20 and a main control device 30.

The motor 20 is configured to drive the fan blades 10 to rotate. The main control device 30 is configured to, after the fan is controlled to enter a scene-wind operation mode, obtain a sleeping time period of a specified user corresponding to the scene-wind operation mode, to obtain a control timing sequence for gears of the fan based on the sleeping time period of the specified user, and to control the fan based on the control timing sequence for gears of the fan to adjust a speed of wind supplied by the fan. The specified user may refer to a special group such as a baby, a pregnant woman, or the like.

In detail, when the specified user such as a baby begins to sleep, parents of the baby or the like may control the fan to enter the scene-wind operation mode via a button, a remote control, a mobile terminal or the like. The remote control may communicate with the fan via wireless communication methods, such as infrared, radio frequency, WiFi.

In an embodiment of the present disclosure, when the main control device 30 is configured to obtain the control timing sequence for gears of the fan based on the sleeping time period of the specified user, the main control device 30 is configured to determine a sleeping state of the specified user based on the sleeping time period of the specified user. The sleeping state of the specified user includes a light sleeping state and a deep sleeping state. When the specified user is in the light sleeping state, the main control device 30 is configured to generate a first control timing sequence for gears by taking a user-set gear as a basic reference variable. When the specified user is in the deep sleeping state, the main control device 30 is configured to generate a second control timing sequence for gears according to the first control timing sequence for gears.

That is, when the specified user such as the baby enters sleep, the light sleeping state may be first entered, and then the deep sleeping state may be entered. When the baby begins to sleep, the parents and the like of the baby may control the fan to enter the scene-wind operation mode via the button, the remote control, the mobile terminal or the like, and an initial gear of the fan is set. At the same time, the main control device 30 may generate the first timing sequence for gears and the second timing sequence for gears by taking the user-set gear as the basic reference variable, and then the fan is controlled according to the first timing sequence for gears and the second timing sequence for gears to adjust the speed of wind supplied by the fan, thus providing soft, comfortable wind speed for the baby during sleeping process of the baby, preventing the baby from catching a cold, and ensuring the baby to have a well sleeping environment.

In an embodiment of the present disclosure, when the specified user is in the light sleeping state, and when the main control device 30 is configured to control the fan based on the first control timing sequence for gears, when the sleeping time period of the specified user reaches a first preset sleeping time period, the main control device 30 is configured to control the fan to operate in a second gear of wind speed, to control the fan to operate in a third gear of wind speed after the fan is controlled to operate in the second gear of wind speed for a first preset time period, to control the fan to operate in the second gear of wind speed for the first preset time period after the fan is controlled to operate in the third gear of wind speed for the first preset time period, and to repeat the controlling process until the sleeping time period of the specified user reaches a second preset sleeping time period. When the sleeping time period of the specified user reaches the second preset sleeping time period, the main control device 30 is configured to control the fan to operate in the second gear of wind speed, to control the fan to operate in the third gear of wind speed after the fan is controlled to operate in the second gear of wind speed for a second preset time period, to control the fan to operate in a first gear of wind speed after the fan is controlled to operate in the third gear of wind speed for the second preset time period, and to control the fan to operate in the first gear of wind speed again after the fan is controlled to operate in the first gear of wind speed for the second preset time period, and repeat the controlling process until the sleeping time period of the specified user reaches a third preset sleeping time period. The second gear of wind speed is greater than the first gear of wind speed and is smaller than the third gear of wind speed.

In addition, after the sleeping time period of the specified user reaches the first preset sleeping time period, the main control device 30 is configured to control the fan to rotate based on a first preset angle.

In detail, when the specified user such as the baby sleeps for 10-20 minutes since the baby begins to sleep, i.e., the sleeping time period of the baby reaches the first preset sleeping time period, the main control device 30 enters the first control timing sequence for gears. As illustrated in FIG. 2a, the main control device 30 first controls the fan to operate in the second gear of wind speed for the first preset time period Δt1, then the fan is controlled to operate in the third gear of wind speed for the first preset time period Δt1, then the fan is controlled to operate in the second gear of wind speed for the first preset time period Δt1, then the fan is controlled to operate in the second gear of wind speed for the first preset time period Δt1, . . . , these processes are repeated until the sleeping time period of the baby reaches the second preset sleeping time period such as 1 hour and 30 minutes. Then, as illustrated in FIG. 2b, the main control device 30 first controls the fan to operate in the second gear of wind speed for the second preset time period Δt2, then the fan is controlled to operate in the third gear of wind speed for the second preset time period Δt2, then the fan is controlled to operate in the first gear of wind speed for the second preset time period Δt2, and then the fan is controlled to operate in the first gear of wind speed for the second preset time period Δt2, . . . , these processes are repeated, and the fan is controlled to rotate based on the first preset angle such as 90°, until the sleeping time period of the baby reaches the third preset sleeping time period, such as 2 hours and 30 minutes. The first preset time period Δt1 and the second preset time period Δt2 may be the same, for example, may be 15 seconds.

In an embodiment of the present disclosure, when the specified user is in the deep sleeping state, and when the main control device 30 is configured to control the fan based on the second control timing sequence for gears, the main control device 30 is configured to control the fan to operate in a second gear of wind speed after the fan is controlled to operate in a first gear of wind speed for a third preset time period, to control the fan to operate in the first gear of wind speed for the third preset time period after the fan is controlled to operate in the second gear of wind speed for the third preset time period, to repeat the controlling process until the sleeping time period of the specified user reaches a fourth preset sleeping time period. When the sleeping time period of the specified user reaches the fourth preset sleeping time period, the main control device 30 is configured to control the fan to operate in the second gear of wind speed, to control the fan to operate in the second gear of wind speed after the fan is controlled to operate in the second gear of wind speed for a fourth preset time period, to control the fan to operate in the first gear of wind speed for the fourth preset time period after the fan is controlled to operate in the second gear of wind speed for the fourth preset time period, and to repeat the controlling process until the sleeping time period of the specified user reaches a fifth preset sleeping time period. When the sleeping time period of the specified user reaches the fifth preset sleeping time period, the main control device 30 is configured to control the fan to operate in the first gear of wind speed, to control the fan to operate in the second gear of wind speed after the fan is controlled to operate in the first gear of wind speed for a fifth preset time period, to control the fan to operate in the first gear of wind speed after the fan is controlled to operate in the second gear of wind speed for the fifth preset time period, and to control the fan to operate in the first gear of wind speed again after the fan is controlled to operate in the first gear of wind speed for the fifth preset time period, and to repeat the controlling process until the sleeping time period of the specified user reaches a sixth preset sleeping time period. The second gear of wind speed is greater than the first gear of wind speed.

In addition, after the sleeping time period of the specified user reaches the sixth preset sleeping time period, the main control device 30 is configured to control the fan to rotate based on a second preset angle, and to control the fan to remain operating in the first gear of wind speed.

In detail, when the specified user such as the baby enters the deep sleeping state, for example, the sleeping time period of the baby reaches the third preset sleeping time period, such as 2 hours and 30 minutes, as illustrated in FIG. 3a, the fan main control device 30 first controls the fan to operate in the first gear of wind speed for the third preset time period Δt3, then the fan is controlled to operate in the second gear of wind speed for the third preset time period Δt3, then the fan is controlled to operate in the first gear of wind speed for the third preset time period Δt3, then the fan is controlled to operate in the first gear of wind speed for the third preset time period Δt3, . . . , these processes are repeated until the sleeping time period of the baby reaches the fourth preset sleeping time period such as 3 hour and 20 minutes. Then, as illustrated in FIG. 3b, the main control device 30 controls the fan to operate in the second gear of wind speed for the fourth preset time period Δt4, then the fan is controlled to operate in the second gear of wind speed for the fourth preset time period Δt4, then the fan is controlled to operate in the first gear of wind speed for the fourth preset time period Δt4, and then the fan is controlled to operate in the first gear of wind speed for the fourth preset time period Δt4, . . . , these processes are repeated until the sleeping time period of the baby reaches the fifth preset sleeping time period such as 4 hour and 10 minutes. And then, as illustrated in FIG. 3c, the main control device 30 controls the fan to operate in the first gear of wind speed for the fifth preset time period Δt5, then the fan is controlled to operate in the second gear of wind speed for the fifth preset time period Δt5, then the fan is controlled to operate in the first gear of wind speed for the fifth preset time period t5, and then the fan is controlled to operate in the first gear of wind speed for the fifth preset time period Δt5, . . . , these processes are repeated for 30 minutes. That is, after the sleeping time period of the baby reaches the sixth preset sleeping time period such as 4 hour and 40 minutes, the fan is controlled to rotate based on the second preset angle such as 120°, and the fan is controlled to remain operating in the first gear of wind speed until the baby wakes up from the sleeping state. The third preset time period Δt3, the fourth preset time period Δt4, and the fifth preset time period Δt5 may be the same, for example, may be 15 seconds.

In an embodiment of the present disclosure, when the specified user is awake from the sleeping state, the main control device 30 is configured to control the fan to operate in a first gear of wind speed, to control the fan to operate in a third gear of wind speed after the fan is controlled to operate in the first gear of wind speed for a sixth preset time period, and to control the fan to operate in a second gear of wind speed for the sixth preset time period after the fan is controlled to operate in the third gear of wind speed for the sixth preset time period, and to repeat the controlling process until the sleeping time period of the specified user reaches a first preset sleeping time period. When the sleeping time period of the specified user reaches the first preset sleeping time period, the main control device 30 is configured to control the fan to operate in the second gear of wind speed, to control the fan to operate in the third gear of wind speed after the fan is controlled to operate in the second gear of wind speed for a seventh preset time period, to control the fan to operate in the first gear of wind speed after the fan is controlled to operate in the third gear of wind speed for the seventh preset time period, and to control the fan to operate in the first gear of wind speed again after the fan is controlled to operate in the first gear of wind speed for the seventh preset time period, and to repeat the controlling process until the fan receives a power-off instruction and the fan is powered off. The second gear of wind speed is greater than the first gear of wind speed and is smaller than the third gear of wind speed.

In addition, after the specified user is awake from the sleeping state, the main control device 30 is configured to control the fan to rotate based on a third preset angle.

In detail, when the specified user such as the baby is awake from the sleeping state, as illustrated in FIG. 4a, the main control device 30 first controls the fan to operate in the first gear of wind speed for the sixth preset time period Δt6, then the fan is controlled to operate in the third gear of wind speed for the sixth preset time period Δt6, then the fan is controlled to operate in the second gear of wind speed for the sixth preset time period Δt6, then the fan is controlled to operate in the second gear of wind speed for the sixth preset time period Δt6, . . . , these processes are repeated until the waking time period of the baby reaches the first preset waking time period such as 1 hour and 30 minutes. Then, as illustrated in FIG. 4b, the main control device 30 controls the fan to operate in the second gear of wind speed for the seventh preset time period Δt7, then the fan is controlled to operate in the third gear of wind speed for the seventh preset time period Δt7, then the fan is controlled to operate in the first gear of wind speed for the seventh preset time period Δt7, and then the fan is controlled to operate in the first gear of wind speed for the seventh preset time period Δt7, . . . , these processes are repeated, and the fan is controlled to rotate based on the third preset angle such as 90°, until the fan is powered off. The sixth preset time period Δt6 and the seventh preset time period Δt7 may be the same, for example, may be 10 seconds.

In some embodiments of the present disclosure, the speed of wind supplied by the fan is greater than or equal to 30 revolutions/minute and is smaller than or equal to 180 revolutions/minute.

Further, in some embodiments of the present disclosure, a speed of wind supplied by the fan corresponding to the first gear of wind speed may be greater than or equal to 30 revolutions/minute and is smaller than or equal to 50 revolutions/minute. A speed of wind supplied by the fan corresponding to the second gear of wind speed may be greater than or equal to 50 revolutions/minute and is smaller than or equal to 100 revolutions/minute. A speed of wind supplied by the fan corresponding to the third gear of wind speed may be greater than or equal to 100 revolutions/minute and is smaller than or equal to 180 revolutions/minute. For example, the main control device 30 may control the motor 20 (such as a direct current frequency conversion motor) in the fan by a rotation speed closed loop control mode to realize the quick start and low speed closed loop control of the fan, and the speed of wind supplied by the fan is compensated by the low speed torque compensation algorithm to ensure stability of the speed of wind supplied by the fan. The direct current frequency conversion motor has advantages of low loss and low noise, thus it may provide the specified user with good sleeping environment, so that the specified user may sleep sweetly.

In addition, when controlling the fan based on the control timing sequence for gears of the fan, the main control device 30 is configured to control the speed of wind supplied by the fan based on above mentioned formula (1). That is, the speed of wind supplied by the fan is controlled based on a damped oscillation curve control algorithm. A corresponding damped oscillation curve may be illustrated in FIG. 5.

The direct current frequency conversion motor is controlled based on the damped oscillation curve control algorithm, so that the speed of wind supplied by the fan is close to a speed of wind shook by a user. That is, a slight wind control is realized, giving comfortable and cool feeling to the specified user such as the baby, the pregnant woman and the like, greatly reducing a probability of catching a cold for the specified user, and low power operation of the direct current frequency conversion motor is realized, achieving effect of energy saving and extending service life.

Figure 7:
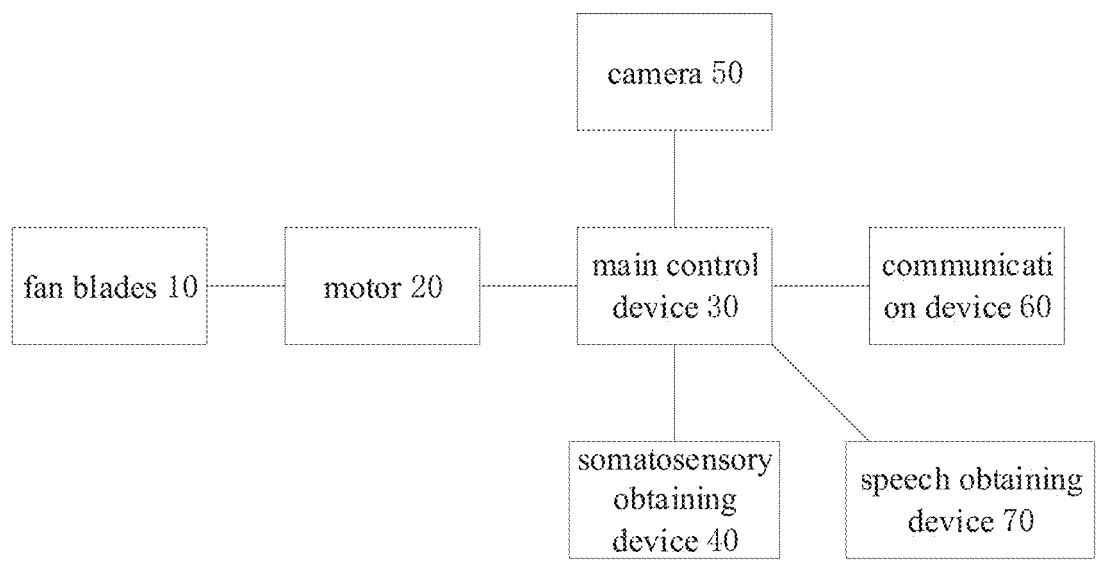
FIG. 7 is a block diagram illustrating a fan according to another embodiment of the present disclosure.

In an embodiment of the present disclosure, as illustrated in FIG. 7, the above mentioned fan further includes a somatosensory obtaining device 40. The somatosensory obtaining device 40 is configured to obtain a human parameter of the specified user. The main control device 30 is configured to generate a wind speed adjusting instruction and a fan-rotating adjusting instruction based on the human parameter of the specified user to adjust the speed of wind supplied by the fan and a rotation angle of the fan.

The human parameter may include body temperature, expression, impatience degree, status, etc. of the specified user. The speed of wind supplied by the fan and the rotation angle of the fan are finely adjusted based on the body parameter of the specified user, so that the speed of wind supplied by the fan and the rotation angle are close to actual needs of the specified user, thereby improving the comfort of the specified user. For example, when the baby is crying, the rotation angle of the fan may be adjusted, such as adjusted between 30° and 180°, to keep the baby away from the fan, and the speed of wind supplied by the fan is adjusted to ensure that the baby may not sweat when crying, not catch a cold, achieving self-adaptation.

In an embodiment of the present disclosure, as illustrated in FIG. 7, the above mentioned fan further includes a camera 50. The camera 50 is configured to obtain image information of the specified user. The main control device 30 is configured to obtain the sleeping state and sleeping quality of the specified user based on the image information of the specified user, and to modify the control timing sequence for gears of the fan based on the sleeping state and the sleeping quality of the specified user. Further, the above mentioned fan further includes a communication device 60. The main control device 30 is configured to send the sleeping state and the sleeping quality of the specified user to a mobile terminal via the communication device 60.

In detail, the image information of the specified user such as the baby may be collected via the camera 50. Then the main control device 30 obtains the sleeping state and sleeping quality of the baby by performing comparison analysis on the image information. The main control device 30 modifies the control timing sequence for gears of the fan based on the sleeping state and the sleeping quality of the baby. The main control device 30 controls the fan according to the modified control timing sequence for gears. At the same time, the main control device 30 may send the sleeping state and sleeping quality of the baby to the mobile terminal, such as a mobile phone, of parents and the like of the baby via the communication device 60. The image information of the baby may also be directly sent to the mobile terminal to realize video sharing, so that the parents and the like of the baby may remotely acknowledge information about the baby in real time, thus the parents and the like of the baby may be more reassured.

In an embodiment of the present disclosure, the above mentioned fan further includes a speech obtaining device 70.

The speech obtaining device 70 is configured to obtain speech information of the specified user. The main control device 30 is configured to send the speech information of the specified user to the mobile terminal via the communication device 60, and to receive speech information from the mobile terminal via the communication device.

In detail, sound of the specified user may be obtained by the speech obtaining device 70 such as a microphone during the sleeping process. The main control device 30 sends the sound of the specified user to a mobile terminal such as a mobile phone of a person relative to the specified user via the communication device 60. For example, when the specified user such as the baby wakes up, the baby may call its parents, at this time, the sound of the baby may be sent to the mobile terminal such as the mobile phone of persons such the parents of the baby or the like. The parents such the parents of the baby or the like may talk to the baby after the parents of the baby or the like receives the call of the baby, to take care of the baby remotely.

With the fan according to embodiments of the present disclosure, after controlling the fan to enter the scene-wind operation mode, the main control device obtains the sleeping time period of the specified user corresponding to the scene-wind operation mode, obtains the control timing sequence for gears of the fan based on the sleeping time period of the specified user, and controls the fan based on the control timing sequence for gears of the fan to adjust the speed of wind supplied by the fan, thus providing soft wind for the specified user during the sleeping process of the user, effectively preventing the specified user from catching a cold due to cold wind, providing a quiet and comfortable sleeping environment for the specified user, and improving sleeping quality of the specified user, with accurate control but without affecting the service life of the fan.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise," "counterclockwise," "axial," "radial," and "circumferential" should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In some embodiments, "a plurality of" means two or more than two, such as two or there, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements.

In the present disclosure, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed there between. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

In the description of the present disclosure, reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

What is claimed is:

1. A method for controlling a fan, the method being implemented by a main control device of the fan, comprising:

obtaining a sleeping time period of a user;
   determining whether the sleeping time period of the user has reached different preset sleeping time periods including a first sleeping period, a second sleeping time period, and a third sleeping time period; and
   when the sleeping time period of the user reaches the first preset sleeping time period, repeatedly performing S1 and S2 in an order of S1, S2, S1 and S1 until the sleeping time period of the user reaches the second preset sleeping time period; and when the sleeping time period of the user reaches the second preset sleeping time period, repeatedly performing S3, S4 and S5 in an order of S3, S4, S5 and S5 until the sleeping time period of the user reaches the third preset sleeping time period, wherein
   S1: controlling the fan to operate in a second wind speed for a first preset time period;
   S2: controlling the fan to operate in a third wind speed for the first preset time period;
   S3: controlling the fan to operate in the second wind speed for a second preset time period;
   S4: controlling the fan to operate in the third wind speed for the second preset time period;
   S5: controlling the fan to operate in a first wind speed for the second preset time period;
   wherein the second wind speed is greater than the first wind speed and smaller than the third wind speed.

2. The method according to claim 1, after the sleeping time period of the user reaches the first preset sleeping time period and before step S1, further comprising:
   controlling the fan to rotate in a first preset angle.

3. The method according to claim 1, further comprising:
   determining whether the sleeping time period of the user has reached different preset sleeping time periods including a fourth sleeping period, a fifth sleeping time period, and a sixth sleeping time period; and when the sleeping time period of the user reaches the third preset sleeping time period, repeatedly performing S6 and S7 in an order of S6, S7, S6 and S6 until the sleeping time period of the user reaches the fourth preset sleeping time period; and when the sleeping time period of the user reaches the fourth preset sleeping time period, repeatedly performing S8 and S9 in an order of S8, S8, S9 and S9 until the sleeping time period of the user reaches the fifth preset sleeping time period; and when the sleeping time period of the user reaches the fifth preset sleeping time period, repeatedly performing S10 and S11 in an order of S10, S11, S10 and S10 until the sleeping time period of the user reaches the sixth preset sleeping time period, wherein S6: controlling the fan to operate in the first wind speed for a third preset time period;

S7: controlling the fan to operate in the second wind speed for the third preset time period;

S8: controlling the fan to operate in the second wind speed for a fourth preset time period;

S9: controlling the fan to operate in the first wind speed for the fourth preset time period;

S10: controlling the fan to operate in the first wind speed for a fifth preset time period;

S11: controlling the fan to operate in the second wind speed for the fifth preset time period.

4. The method according to claim 3, after the sleeping time period of the user reaches the sixth preset sleeping time period, further comprising:

controlling the fan to rotate in a second preset angle, and controlling the fan to remain operating in the first wind speed.

5. The method according to claim 1, further comprising:

detecting, by a speech obtaining device, that the user is awake from the sleeping state;

obtaining a waking time period of the user;

determining whether the waking time period of the user has reached a first preset waking time period; and repeatedly performing S13, S14 and S15 in an order of S13, S14, S15 and S15 until the waking time period of the user reaches the first preset waking time period; and when the waking time period of the user reaches the first preset waking time period, repeatedly performing S16, S17 and S18 in an order of S16, S17, S18 and S18 until the fan receives a power-off instruction and the fan is powered off, wherein S13: controlling the fan to operate in the first wind speed for a sixth preset time period;

S14: controlling the fan to operate in the third wind speed for the sixth preset time period;

S15: controlling the fan to operate in the second wind speed for the sixth preset time period;

S16: controlling the fan to operate in the second wind speed for a seventh preset time period;

S17: controlling the fan to operate in the third wind speed for the seventh preset time period;

S18: controlling the fan to operate in the first wind speed for the seventh preset time period.

6. The method according to claim 5, after the user is awake from the sleeping state and before step S13, further comprising:

controlling the fan to rotate in a third preset angle.

7. The method according to claim 1, wherein each of the first, second and third wind speed is greater than or equal to 30 revolutions/minute and is smaller than or equal to 180 revolutions/minute.

8. The method according to claim 1, further comprising: obtaining a human parameter of the specified user, and generating a wind speed adjusting instruction and a fan-rotating adjusting instruction based on the human parameter of the specified user to adjust the speed of wind supplied by the fan and a rotation angle of the fan.

9. The method according to claim 1, further comprising: obtaining image information of the user, obtaining a sleeping state and a sleeping quality of the user based on the image information of the user, and modifying a control timing sequence of the fan based on the sleeping state and the sleeping quality of the user.

10. The method according to claim 9, further comprising: sending the sleeping state and the sleeping quality of the user to a mobile terminal.

11. The method according to claim 10, further comprising: obtaining speech information of the user, sending the speech information of the user to the mobile terminal, and receiving speech information from the mobile terminal.

* * * * *